(12) United States Patent
Saw et al.

(10) Patent No.: US 11,744,570 B2
(45) Date of Patent: Sep. 5, 2023

(54) PATELLA JOYSTICK AND METHOD OF USE THEREOF

(71) Applicants: Khay Yong Saw, Kuala Lumpur (MY); Reza Ching Soong Ng, Kuala Lumpur (MY); Caroline Siew Yoke Jee, Kuala Lumpur (MY)

(72) Inventors: Khay Yong Saw, Kuala Lumpur (MY); Reza Ching Soong Ng, Kuala Lumpur (MY); Caroline Siew Yoke Jee, Kuala Lumpur (MY)

(*) Notice: Subject to any disclaimer, the term of this patent is extended or adjusted under 35 U.S.C. 154(b) by 170 days.

(21) Appl. No.: 17/193,627

(22) Filed: Mar. 5, 2021

(65) Prior Publication Data

US 2021/0275158 A1     Sep. 9, 2021

Related U.S. Application Data

(60) Provisional application No. 62/987,116, filed on Mar. 9, 2020.

(51) Int. Cl.
| | | |
|---|---|---|
| *A61B 17/02* | (2006.01) | |
| *A61B 1/317* | (2006.01) | |
| *A61B 17/16* | (2006.01) | |
| *A61B 17/00* | (2006.01) | |

(52) U.S. Cl.
CPC ............ *A61B 17/025* (2013.01); *A61B 1/317* (2013.01); *A61B 17/1677* (2013.01); *A61B 2017/0046* (2013.01); *A61B 2017/00424* (2013.01); *A61B 2017/0268* (2013.01)

(58) Field of Classification Search
CPC ............... A61B 1/317; A61B 17/1677; A61B 2017/0268; A61B 17/025
See application file for complete search history.

(56) References Cited

U.S. PATENT DOCUMENTS

| 4,862,881 A | 9/1989 | Shea | |
|---|---|---|---|
| 5,129,901 A | 7/1992 | Decoste | |
| 2006/0084992 A1* | 4/2006 | Michelson | ......... A61B 17/1757 606/86 R |
| 2006/0241633 A1* | 10/2006 | Stalcup | ............... A61B 17/025 606/86 R |

(Continued)

OTHER PUBLICATIONS

International Search Report issued in International Application No. PCT/MY2021/050013, dated Jun. 29, 2021, 5 pages.

(Continued)

*Primary Examiner* — Christian A Sevilla
(74) *Attorney, Agent, or Firm* — Hamre, Schumann, Mueller & Larson, P.C.

(57) ABSTRACT

The disclosure provides a patella joystick for tilting a knee cap in an operation of knee arthroscopy and a method of using the patella joystick. The patella joystick can include a handle, a shank, a tapered portion, and a screw portion. The tapered portion has a diminishing diameter and provides a structural transition between the shank and the screw portion. The screw portion can include a thread and a screw point. The thread can have a buttress form, and the screw point can have an inverted cone shape with a cone angle of at or about 90°. The method of using the patella joystick can include: drilling a pilot hole into the patella; screwing the patella joystick onto the pilot hole; and holding the patella joystick to tilt and/or lift the knee cap.

20 Claims, 5 Drawing Sheets

(56) References Cited

U.S. PATENT DOCUMENTS

| | | |
|---|---|---|
| 2007/0213730 A1 | 9/2007 | Martinek et al. |
| 2010/0030065 A1* | 2/2010 | Farr ................. A61B 17/025 606/279 |
| 2010/0198354 A1 | 8/2010 | Halbrecht |
| 2014/0207233 A1* | 7/2014 | Steiner ............ A61B 17/8875 623/13.14 |
| 2015/0173733 A1* | 6/2015 | Ryshkus ........... A61B 17/0218 600/235 |
| 2018/0263670 A1 | 9/2018 | Moctezuma De la Barrera et al. |
| 2019/0046217 A1* | 2/2019 | Rasmussen ....... A61B 17/1764 |
| 2019/0343640 A1* | 11/2019 | Donner .............. A61F 2/4405 |

OTHER PUBLICATIONS

Written Opinion of the International Search Authority issued in International Application No. PCT/MY2021/050013, dated Jun. 29, 2021, 6 pages.

\* cited by examiner

PATELLA JOYSTICK AND METHOD OF USE THEREOF

FIELD

The disclosure generally relates to knee arthroscopy. Specifically, the disclosure relates to a medical tool for knee arthroscopy. More specifically, the disclosure relates to a patella joystick for tilting and/or lifting a patella in knee arthroscopy and a method of using thereof.

BACKGROUND

The patella is also known as the knee cap. The arthroscopy, also called the arthroscopic or keyhole surgery, is a surgical technique for examining, diagnosing, and sometimes treating damage in a joint due to conditions such as, for example, injury, inflammation, etc. The joint can be a knee, shoulder, elbow, ankle, hip, or wrist.

SUMMARY

The embodiments herein provide a patella joystick for knee arthroscopy. The patella joystick has an elongated body including a shank portion, a tapered portion, and a screw portion. The tapered portion is disposed between the shank portion and the screw portion. The tapered portion includes a frustum having a first end and a second end opposing the first end, and the first end faces and joins the shank portion. The screw portion includes a thread and a screw point.

In an embodiment, the elongated body is irremovably or removably attached to a handle or a screw bit holder.

In an embodiment, the screw portion has a length of at or about 3 mm to at or about 70 mm, the thread has a depth of at or about 0.1 mm to at or about 2 mm, and the thread has a pitch of at or about 0.1 mm to at or about 5 mm. In an embodiment, the thread has a buttress thread form.

In an embodiment, the screw portion has a cut at its distal end. In an embodiment, the cut forms a flute having a cutting edge.

In an embodiment, the screw point has an inverted cone shape with a point angle of at or about 90°.

In an embodiment, the tapered portion further includes a reduced part extending from the second end of the frustum and is smaller in diameter or thickness than the second end of the frustum.

In an embodiment, the frustum has a vertical angle in a range of at or about 1 to at or about 89 degrees. In an embodiment, the frustum has a length of at or about 1 mm to at or about 150 mm.

In an embodiment, the shank portion has a diameter or thickness in a range of at or about 2 mm to at or about 20 mm. In an embodiment, the shank portion and the tapered portion has a total length of at or about 70 mm.

The embodiments also provide a method for performing a knee arthroscopy using the patella joystick. The method includes screwing the patella joystick onto a knee cap. In an embodiment, the method further includes drilling a pilot hole at an approximate center of the knee cap. In an embodiment, the pilot hole has a diameter of at or about 2 mm and a depth of not more than 20 mm. In an embodiment, the method further includes performing a cut through the skin at an approximate center of the knee cap. In an embodiment, the method further includes holding the patella joystick to tilt and/or lift the knee cap for performing an arthroscopy procedure. In an embodiment, the arthroscopy procedure includes performing subchondral drilling or debriding on the cartilage of the knee cap.

BRIEF DESCRIPTION OF THE DRAWINGS

References are made to the accompanying drawings that form a part of this disclosure, and which illustrate embodiments in which the device and method described in this specification can be practiced.

Like reference numbers represent like parts throughout different views and embodiments.

DETAILED DESCRIPTION

This disclosure provides a patella joystick for tilting and/or lifting a knee cap in knee arthroscopy. This disclosure also provides a method of using the patella joystick in knee arthroscopy.

The term "a", "an", or "the" cover both the singular and the plural reference, unless the context dictates otherwise. The terms "comprising", "having", "including", and "containing" are open-ended terms, which means "including but not limited to", unless otherwise indicated.

Certain values herein are preceded by the term "about". The term "about" herein provides literal support for the exact value that it precedes, as well as a range that is near to or approximately the value that the term precedes. In an embodiment, the range is from 70% to 130% of the exact value that the term "about" precedes. In an embodiment, the range is from 80% to 120% of the exact value that the term "about" precedes. In an embodiment, the range is from 90% to 110% of the exact value that the term "about" precedes. In an embodiment, the range is from 99% to 101% of the exact value that the term "about" precedes. For example, if the exact value is 100, the range from 70% to 130% of the exact value is 70 to 130.

The term "thickness" refers to the width or thickness of a three-dimensional object described herein.

Knee arthroscopy is an arthroscopic knee surgical technique. Knee arthroscopy can be used to diagnose and treat knee disorders and injuries such as, for example, torn anterior or posterior cruciate ligaments, torn meniscus, misaligned patella, pieces of torn cartilage that are loose in the joint, subchondral drilling, swollen synovium, and the like. Knee arthroscopy can be a minimally invasive surgical procedure and usually results in less joint pain and better outcome than the traditional "open" surgery.

During the arthroscopic knee surgery, a surgeon may make one or more small openings or ports, and then insert an arthroscopy having, for example, a small fiber-optic camera, into the knee through the small opening(s) or port(s). This allows the surgeon to visually check the inside of the knee from, for example, a screen. The surgeon can then investigate a problem with the knee and, if necessary, correct the problem using, for example, a miniature instrument within the arthroscope.

The undersurface of the knee cap is covered with a layer of smooth cartilage. In some instances, the knee arthroscopy may involve tilting and/or lifting the knee cap for subchondral drilling on the cartilage of the knee cap, checking or debriding the cartilage of the knee cap, and the like. Normally, an operator such as a surgeon, nurse, or assistant uses his/her bare hand to hold the skin around the knee cap and then tilt and/or lift the knee cap. This can be a problem, as it is difficult or, in some situations, not practical for the operator to use his/her bare hand to tilt and/or lift the knee cap while operating the knee arthroscopy.

Figure 1:
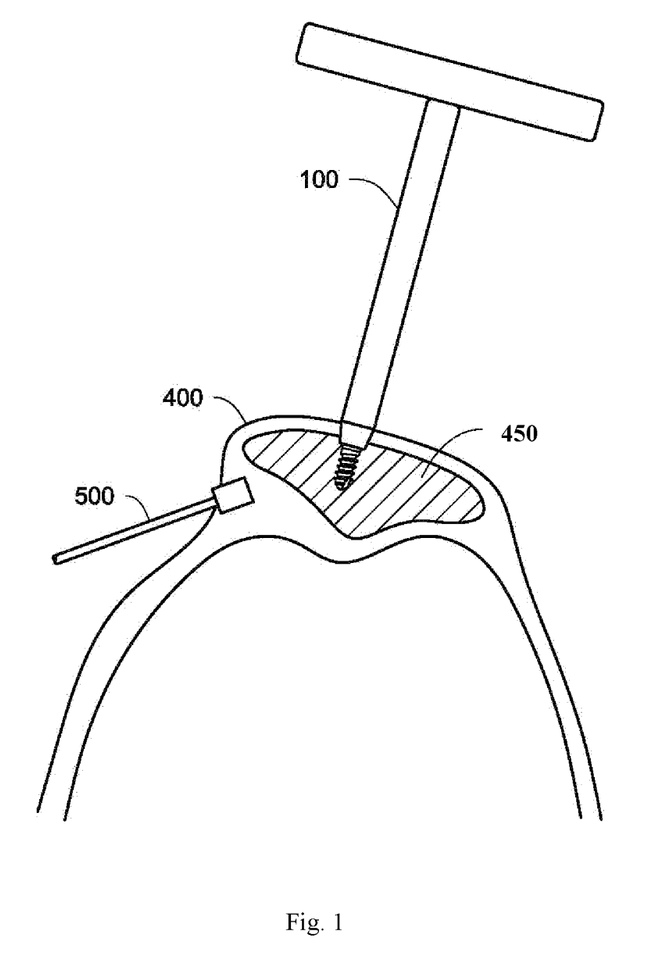
FIG. 1 schematically illustrates the use of a patella joystick to tilt and/or lift the patella bone in arthroscopic knee surgery, according to an embodiment.

The patella joystick described herein exhibits significant advantages over the bare hand for tilting and/or lifting the knee cap in the knee arthroscopy. Referring to FIG. 1, the patella joystick 100 is secured on the knee cap 450 of a knee 400. In an embodiment, the patella joystick 100 is screwed onto the knee cap 450. An arthroscopy 500 is inserted inside the knee 400 from an area neighboring the knee cap 450. The operator can hold the patella joystick 100 to tilt and/or lift the knee cap 450 for performing, for example, subchondral drilling or debriding on the cartilage of the knee cap using the arthroscopy 500. The patella joystick 100 provides the operator with the benefits of easiness and convenience for tilting/and lifting the knee cap in such knee arthroscopy.

Figure 2A:
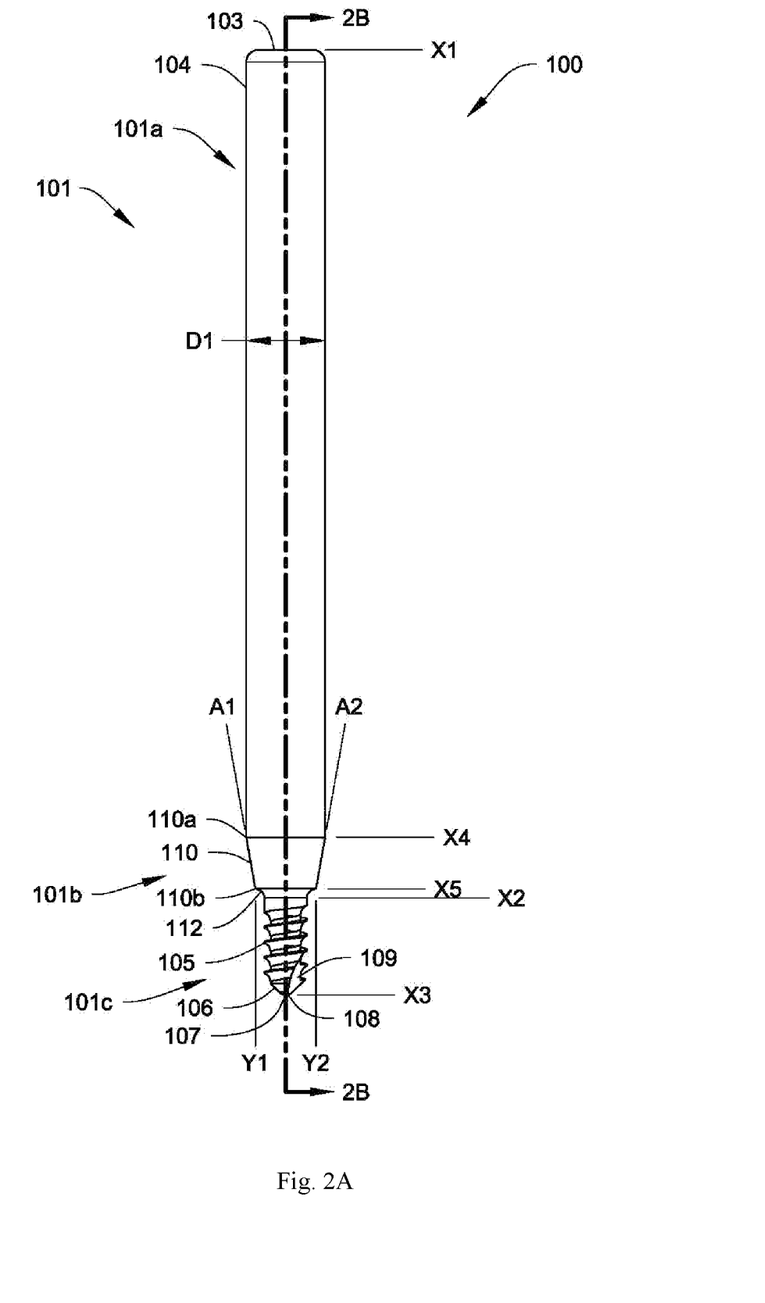
FIG. 2A schematically illustrates an embodiment of the patella joystick, according to an embodiment.

Referring to FIG. 2A, FIG. 2A illustrates an embodiment of the patella joystick 100. This embodiment can include an elongated body 101 having an end 103 and an end 108 opposing the end 103. The body 101 can include a shank portion 101a, a tapered portion 101b, and a screw portion 101c in order from the end 103 to the end 108.

The shank portion 101a can adopt any shape capable of forming a shank. In an embodiment, the shank portion 101a has a regular shape. In an embodiment, the shank portion 101a has an irregular shape. In an embodiment, the shank portion 101a has a rod configuration. In an embodiment, the shank portion 101a is a cylindrical rod, triangular rod, square rod, rectangular rod, pentagonal rod, hexagonal rod, octagonal rod, or the like, or a combination thereof.

The shank portion 101a can have a length, e.g., the most extended dimension defined by the distance between lines X1 and X4, suitable for a surgeon to drive the screw portion 101c into the knee cap. In an embodiment, the length can be in a range of at or about 10 mm to at/or about 140 mm. In an embodiment, the upper limit of the range of the length can be at/or about 140 mm, at/or about 120 mm, at or about 100 mm, at or about 80 mm, or at or about 60 mm. In an embodiment, the lower limit of the range of the length can be at or about 15 mm, at or about 20 mm, at or about 25 mm, at or about 30 mm, or at or about 35 mm.

The shank portion 101a can have a diameter or thickness indicated by D1, e.g., the dimension extends perpendicular to its length direction, in a range of at or about 2 mm to at or about 20 mm. In an embodiment, the upper limit of the range of diameter or thickness can be at or about 17 mm, at or about 14 mm, or at or about 11 mm. In an embodiment, the lower limit of the range of diameter or thickness can be at or about 3 mm, at or about 5 mm, at or about 7 mm, or at or about 9 mm.

In an embodiment, the shank portion 101a can fit into a screw bit holder so that an operator can use a T-handle driver or a screwdriver, for example, a hand-held screwdriver or torque screwdriver, to rotate and insert the screw portion 101c to the knee cap. In an embodiment, the distal end 104 of the shank portion 101a can include a triangular, square, pentagonal, hexagonal, octagonal structure, or the like, or a combination thereof, so that the shank portion 101a can be secured into the screw bit holder.

The screw portion 101c can include a thread 105 for securing the patella joystick 100 onto the knee cap. In an embodiment, the thread 105 is capable of converting rotational force to linear movement. The thread 105 can include a right-handed thread or left-handed thread. In an embodiment, the thread 105 includes a right-handed thread. In an embodiment, the thread 105 includes a male thread.

The thread 105 can adopt various suitable forms that include but not limited to, for example, type A, type AB, type B, type F, type 23, type 17, type 25, type 2, type 3, or the like, or a combination thereof. In an embodiment, the thread 105 includes a self-drilling screw. In an embodiment, the thread 105 includes a self-taping screw. The thread of the self-taping screw can be precisely angled so that, once the screw portion 101c is screwed onto the knee cap, the thread will not slip or move unless some additional force is applied. The self-tapping screw can include but not limited to, for example, type A self-tapping screw, type AB self-tapping screw, type B self-tapping screw, Hi-Lo self-tapping screw, or the like, or a combination thereof. In an embodiment, the thread 105 includes a self-tapping locking screw.

In an embodiment, the screw portion 101c includes a transition 106 extending between the distal end of the thread 105 and the end 108. In an embodiment, the transition 106 includes a screw point 107. In an embodiment, the transition 106 is a screw point 107. In an embodiment, the transition 106 includes a pilot section. In an embodiment, the transition 106 includes both the pilot section and the screw point 107, and the pilot section extends between the distal end of the thread 105 and the screw point 107. The transition 106 can be useful for providing a structural transition from the thread 105 to the end 108, as well as ensuring proper hole alignment. The transition 106 can be optional. In an embodiment, the screw portion 101c does not include a transition 106, and the distal end of the thread 105 is the end 108.

In an embodiment, the screw portion 101c has a cut 109 at its distal end. In an embodiment, the cut 109 extends from the end 108 to a portion of the thread 105. In an embodiment, the cut 109 forms a flute having a cutting edge useful for screwing the patella joystick 100 onto the knee cap.

The screw portion 101c can have a length suitable for securing the patella joystick 100 onto the knee cap. The length can be defined by the distance between lines X2 and X3. The length can be in a range of at or about 3 mm to at or about 70 mm. In an embodiment, the length is in a range of at or about 3 mm to 50 mm. In an embodiment, the length is in a range of at or about 3 mm to 10 mm.

The screw portion 101c can have a thread diameter in a range of at or about 0.5 mm to at or about 5 mm. In an embodiment, the thread diameter is in a range of at or about 0.5 mm to at or about 4 mm. In an embodiment, the thread diameter is in a range of at or about 0.5 mm to at or about 3 mm. In an embodiment, the thread diameter is at or about 3.5 mm.

The end 108 can be a blunt end or sharp end. The sharp end can include a sharp edge useful for drilling into the knee cap. The blunt end can include a blunt edge. The blunt edge can include but not limited to, for example, a flat edge, rounded edge, or the like, or a combination thereof.

The tapered portion 101b is disposed between the shank portion 101a and the screw portion 101c. The tapered portion 101b can have a decreasing diameter or thickness while extending from the shank portion 101a to the screw portion 101c. As the screw portion 101c generally has a diameter smaller than the diameter or thickness of the shank portion 101a, the tapered portion 101b can provide a transition in the diameters or thickness from the shank portion 101a to the screw portion 101c. In an embodiment, the tapered portion 101b avoids dragging the skin layer while the patella joystick 100 is being screwed through the skin.

In an embodiment, the tapered portion 101b includes an inverted frustum 110 and a reduced part 112. In an embodiment, the inverted frustum 110 is an inverted, truncated cone. The inverted frustum 110 has a first end 110a and a second end 110b opposing the first end 110a. The first end 110a is larger in diameter or thickness than the second end 110b. The first end 110a faces and joins the shank portion 101a, and the second end 110b faces and joins the reduced part 112.

The inverted frustum 110 can have a vertical angle, which is the angle between lines A1 and A2, in a range of at or about 1 degree to at or about 89 degrees, according to an embodiment. In an embodiment, the vertical angle is at or about 20°.

The inverted frustum 110 can have a length defined by the distance between lines X4 and X5 in a range of at or about 1 mm to at or about 150 mm. In an embodiment, the length is at or about 1 mm to at or about 5 mm. In an embodiment, the length is at or about 2 mm to at or about 4 mm. In an embodiment, the length is at or about 3 mm.

The first end 110a of the inverted frustum 110 can have a diameter or thickness identical to that of the shank portion 110a. The second end 110b of the inverted frustum 110 can have a diameter or thickness, which is defined by the distance between lines Y1 and Y2, in a range of at or about 1 mm to at or about 20 mm.

The reduced part 112 can have a diameter or thickness smaller than that of the second end 110b of the inverted frustum 110. In an embodiment, the reduced part 112 has a diameter or thickness close to or identical to the diameter of the screw portion 101c. In an embodiment, the reduced part 112 can have a diameter or thickness in a range of at or about 0.1 mm to at or about 3 mm.

The reduced part 112 can also have a length indicated by lines X5 and X2 in a range of at or about 0.5 mm to at or about 50 mm. In an embodiment, the length of the reduced part 112 is in a range of 0.5 mm to 10 mm. In an embodiment, the length is in a range of 0.5 mm to 8 mm. In an embodiment, the length is in a range of 0.5 mm to 3 mm.

It is to be understood that one or more of the features may be optional. In an embodiment, the reduced part 112 can be optional. In an embodiment, the inverted frustum 110 is optional. In an embodiment, the tapered portion 101b is optional. In an embodiment, the patella joystick 100 does not include the tapered portion 101b, and the patella joystick 100 undergoes a sudden change in the diameter or thickness from the shank portion 101a to the screw portion 101c. In an embodiment, the shank portion 101a is optional. In an embodiment, the patella joystick 100 does not include the shank 101a, and the tapered portion 101b is long enough to function as a shank.

Figure 2B:
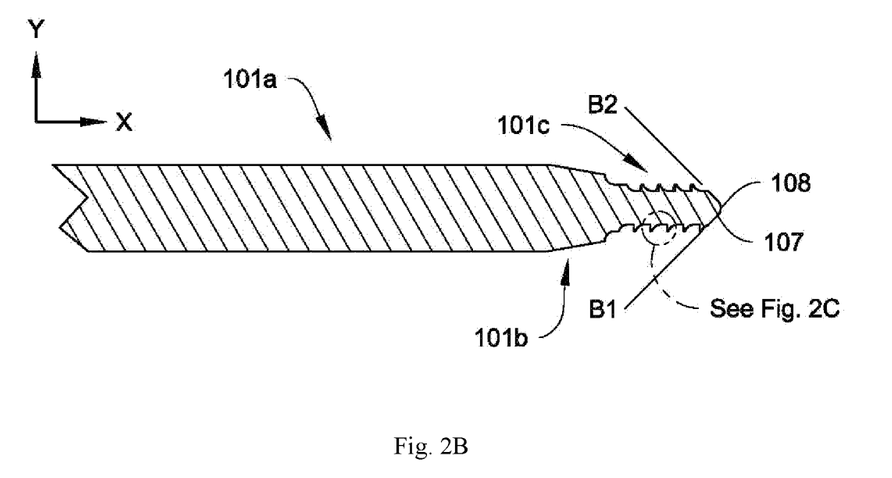
FIG. 2B schematically illustrates the A-A section of the patella joystick of FIG. 2A, according to an embodiment.

Referring to FIG. 2B, FIG. 2B schematically illustrates the A-A section of the patella joystick 100 of FIG. 1A, according to an embodiment. The A-A section is along the central axis of the patella joystick 100. The tapered portion 101b can generally have a decreasing thickness while extending from shank portion 101a to the screw portion 101c. In an embodiment, the tapered portion 101b gradually reduces the diameter of the shank portion 101a to that of the screw portion 101c. In an embodiment, the tapered portion 101b provides a smooth transition in diameter from the shank portion 101a to the screw portion 101c.

The screw portion 101c can include the screw point 107, according to an embodiment. The screw point 107 can be configured to various styles or shapes including but not limited to, for example, cone, oval, plain cup, flat, half-dog, soft-tipped, and knurled cup, or the like, or a combination thereof. In an embodiment, the screw point 107 adopts an inverted cone shape and has a point angle, e.g., the cone angle between lines B1 and B2, in a range of at or about 1° to at or about 160°. In an embodiment, the cone angle is at or about 90°. In an embodiment, the distal end of the screw point 107 is the end 108. The screw point 107 can have a length in a range of at or about 1 mm to at or about 10 mm.

The elongation direction of the screw portion 101c is aligned with the X-axis of the paper plane of FIG. 2B. The thickness direction of the screw portion 101c is aligned with the Y-axis of the paper plane of FIG. 2B.

Figure 2C:
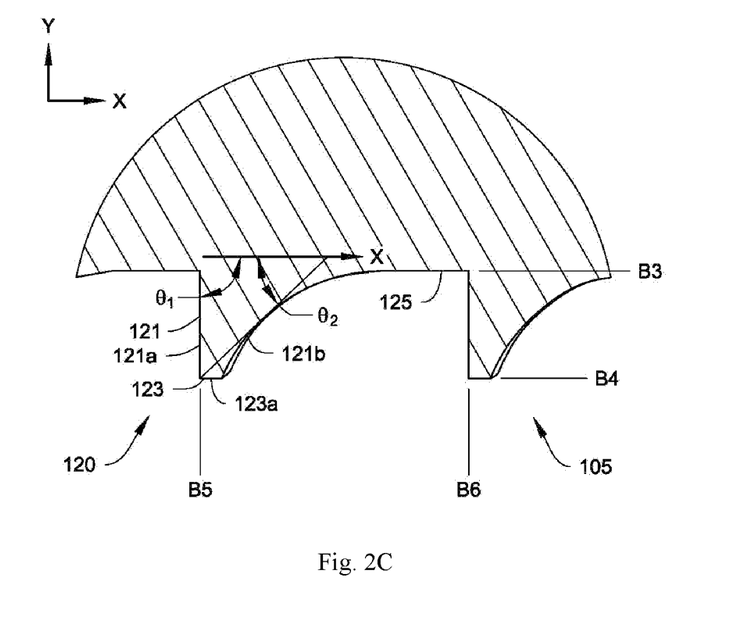
FIG. 2C schematically illustrates an enlarged view of the portion B of FIG. 2B, according to an embodiment.

Referring to FIG. 2C, FIG. 2C is an enlarged view of the portion B of FIG. 2B. FIG. 2C illustrates the thread 105 of the screw portion 101c. The thread 105 can include screw thread 120. The screw thread 120 can include flank 121, crest 123, and root 125. The flank 121 can be the portion of the surface on either side of the screw thread 120. The root 125 can be the bottom edge of the screw thread 120, connecting the adjacent flank 121 at the bottom of the screw thread 120. The crest 123 can be the peak edge of the screw thread 120, connecting the adjacent flank 121 at the top of the thread 105.

The crest 123 can include a surface 123a. The surface 123a can be a flat surface, a curved surface, a sharp edge, or a combination thereof. In an embodiment, the surface 123a is a flat surface. In an embodiment, the surface 123a is a round surface. In an embodiment, the surface 123a is a sharp edge.

The flank 121 can have a driving side 121a and a back side 121b. The driving side 121a and the back side 121b can intersect X-axis, i.e., the elongation direction of the screw portion 101c, at angles $\theta_1$ and $\theta_2$, respectively. Each of $\theta_1$ and $\theta_2$ can be in a range of large than 0° and less than 180°. $\theta_1$ can be identical to or different from $\theta_2$. In an embodiment, both $\theta_1$ and $\theta_2$ are 90°. In an embodiment, both $\theta_1$ and $\theta_2$ are less than 90°.

The flank 121 can be non-symmetric. That is, the driving side 121a and the back side 121b are not related to each other by mirror symmetry. In an embodiment, the thread 105 can have a buttress thread form, in which $\theta_1$ is 90° and $\theta_2$ is less than 90°. That is, the driving side 121a is perpendicular to the elongation direction of the screw portion 101c, and the back side 121b makes an oblique angle with the elongation direction. The crest 123 of the buttress thread form can include a flat surface. The buttress thread form is also known as the breech-lock thread form, which can be useful for locking the patella joystick 100 onto the knee cap and improve the pull-out load of the patella joystick 100.

The flank 121 can also be symmetric. In an embodiment, the thread 105 can have a square thread form, in which both $\theta_1$ and $\theta_2$ are equal to 90°. That is, both the driving side 121a and the back side 121b are perpendicular to the elongation direction of the screw portion 101c. The crest 123 of the square thread form can be a flat surface.

In an embodiment, the thread 105 can have a trapezoidal thread form, in which both the driving side 121a and the back side 121b make an oblique angle to the elongation direction of the screw portion 101c. In an embodiment, the thread 105 can have a round thread form, in which the crest 123 is a smooth curved surface.

The thread 105 can have a pitch, which is indicated by the distance between lines B5 and B6, in a range of at or about 0.1 mm to at or about 5 mm. In an embodiment, the thread 105 can have a pitch of at or about 1.25 mm.

The thread 105 can have a depth, which is indicated by the distance between lines B3 and B4, in a range of at or about 0.1 mm to at or about 2 mm. In an embodiment, the thread 105 can have a depth of at or about 0.5 mm.

Figure 3A:
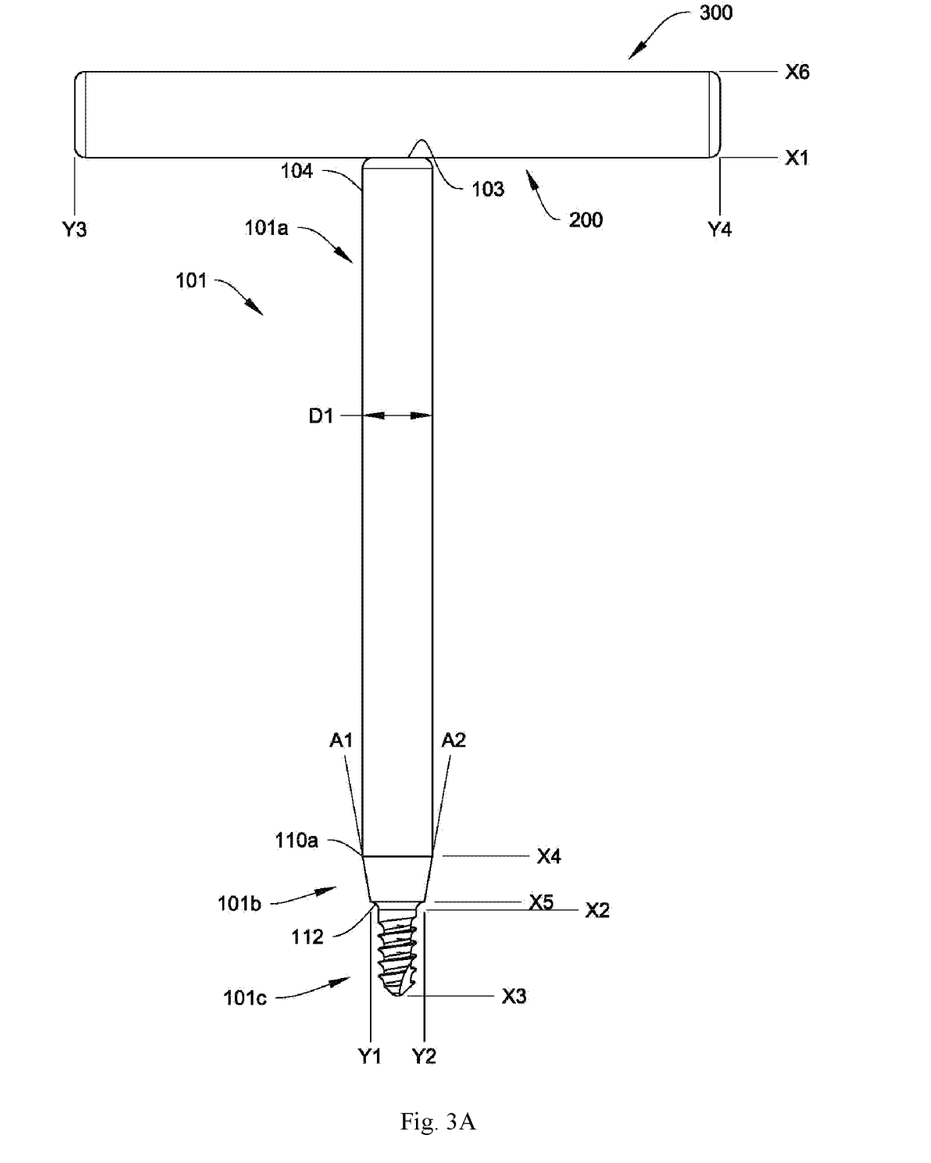
FIG. 3A schematically illustrates a patella joystick, according to another embodiment.

Referring to FIG. 3A, FIG. 3A schematically illustrates a patella joystick 300 according to another embodiment. This embodiment can include features of the patella joystick 100 discussed above. For simplicity of this Specification, features which are the same are labeled with like reference numbers and are not described in further detail. The patella joystick 300 can include a handle 200 in addition to the shank portion 101a, the tapered portion 101b, and the screw portion 101c.

The handle 200 can adopt a structure and shape useful for rotating and tilting the body 101. In an embodiment, the handle 200 can have an elongated body. In an embodiment, the handle 200 includes a knob. In an embodiment, the handle is a knob. In an embodiment, the handle 200 is a screwdriver handle. In an embodiment, the handle 200 has a regular shape. In an embodiment, the handle 200 has an irregular shape. In an embodiment, the handle 200 has a rod configuration including but not limited to, for example, a cylindrical rod, triangular rod, square rod, rectangular rod, pentagonal rod, hexagonal rod, or octagonal rod, or the like, or a combination thereof. In an embodiment, the handle 200 is a straight rod. In an embodiment, the handle 200 is a curved rod. The handle 200 is capable of being attached to the shank portion 101a of the body 101. In an embodiment, the patella joystick 300 has a "T" configuration. In an embodiment, the patella joystick 300 can have a configuration other than the "T" configuration, for example, a screwdriver configuration.

The handle 200 can have a length, which is indicated by line Y3 and Y4, in a range from at or about 20 mm to at or about 200 mm, according to an embodiment. In an embodiment, the handle 200 has a length of no more than 30 mm, 40 mm, 50 mm, 60 mm, 70 mm, or 80 mm. In an embodiment, the handle 200 can have a length of at or about 60 mm. In an embodiment, the handle 200 can have a diameter or thickness, which is indicated by lines X6 and X1, in a range of at or about 1 mm to at or about 100 mm.

In an embodiment, the handle 200 can have a diameter of at or about 8 mm. In an embodiment, the handle 200 can have a diameter of at or about 6 mm. In an embodiment, the handle 200 can have a diameter of at or about 4 mm.

The shank portion 101a can be secured to the handle 200 for rotating the screw portion 101c into the knee cap. In an embodiment, the shank portion 101a removably attaches to the handle 200 via its end 103. In an embodiment, the end 103 is removably attached to the handle 200 via a structure, for example, a hole, on the handle 200. In another embodiment, the shank portion 101a irremovably attaches to the handle 200 via its end 103. In an embodiment, the end 103 is welded to the handle 200. In an embodiment, the shank portion 101a and the handle 200 are unitary one-piece construction, e.g., being machined from a single piece of material.

In an embodiment, the shank portion 101a has a diameter of at or about 6.5 mm. In an embodiment, the shank portion 101a has a diameter of at or about 5 mm. In an embodiment, the shank portion 101a has a diameter of at or about 4 mm. In an embodiment, the shank portion 101a has a diameter of 2 mm.

The tapered portion 101b includes the inverted frustum 110 and the reduced part 112. The inverted frustum 110 can be an inverted, truncated cone. In an embodiment, the inverted frustum 110 can have a length of at or about 4.25 mm indicated by lines X4 and X5. In an embodiment, the inverted frustum 110 can have a cone angle of at or about 20° indicated by lines A1 and A2. In an embodiment, the inverted frustum 110 has a cone angle no more than at or about 89°. In an embodiment, the distal end of the inverted frustum 110 can have a diameter of at or about 5 mm to at or about 5.75 mm, defined by the distance between lines Y1 and Y2. In an embodiment, the shank portion 101a and the tapered portion 101b can have a total length of at or about 70 mm, which is indicated by lines X1 and X2. In an embodiment, the shank portion 101a and the tapered portion 101b has a total length in a range from at or about 70 mm to at or about 150 mm. In an embodiment, the screw portion 101c of the patella joystick 300 can have a length of at or about 8 mm indicated by lines X2 and X3.

Figure 3B:
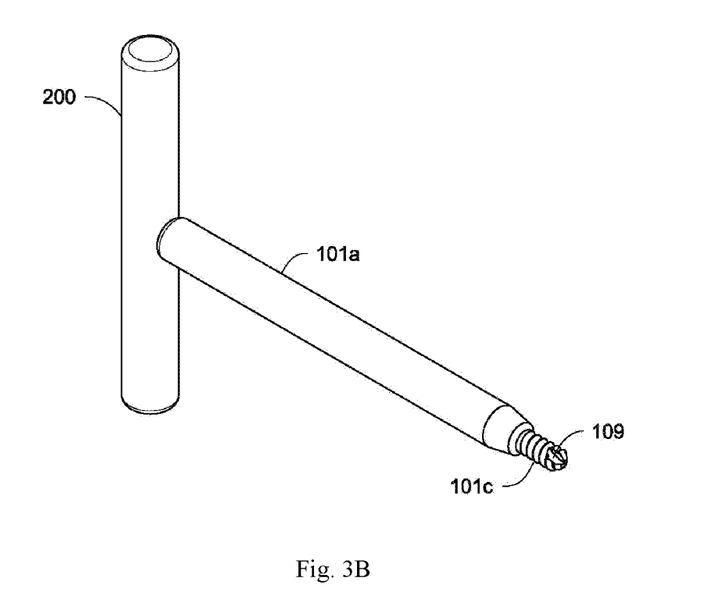
FIG. 3B is a perspective view of the patella joystick of FIG. 3A, according to an embodiment.

Referring to FIG. 3B, FIG. 3B schematically illustrates a perspective view of the patella joystick 300 of FIG. 3A, according to an embodiment. The handle 200 can be a cylindrical pipe. The shank 101a can attach to the middle of the handle 200. The screw portion 101c includes the cut 109.

Figure 3C:
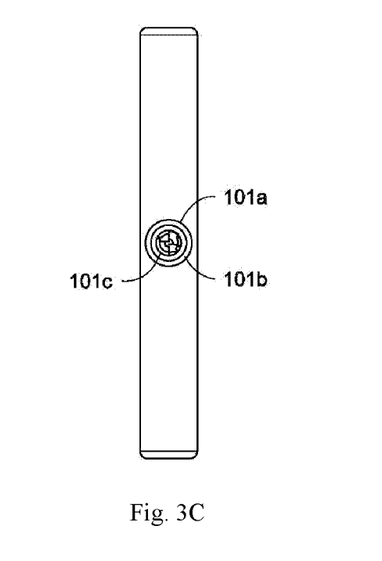
FIG. 3C is a bottom view of the patella joystick of FIG. 3A, according to an embodiment.

Referring to FIG. 3C, FIG. 3C schematically illustrates a bottom view of the patella joystick 300 of FIG. 3A, according to an embodiment. The shank portion 101a can be cylindrical. The axes of the shank portion 101a, the tapered portion 101b, and the screw portion 101c are aligned together. That is, the shank portion 101a, the tapered portion 101b, and the screw portion 101c coaxially extend.

Each of the shank portion 101a, the tapered portion 101b, the screw portion 101c, and the handle 200 can independently be made from a material with suitable strength, hardness, and/or rigidity. In an embodiment, the material can include a metal including but not limited to, for example, surgical-grade metal alloys, stainless steel, chrome-molybdenum vanadium steel, carbon steel, titanium alloy, or the like, or a combination thereof. In an embodiment, the material can include a plastic material including but not limited to, for example, polymethylmethacrylate (PMMA), polyetherketoneketone (PEKK), polyetheretheketone (PEEK), polyaryletherketone (PAEK), or the like, or a combination thereof. It will be appreciated that the material can also include but not limited to, for example, porcelain, glass, composite material, or the like, or a combination thereof. In an embodiment, the material is an autoclavable material.

In an embodiment, two or more of the shank portion 101a, the tapered portion 101b, the screw portion 101c, and the handle 200 can be machined from a single piece of material. In an embodiment, the shank portion 101a, the tapered portion 101b, the screw portion 101c, and the handle 200 are machined from a single piece of material. In an embodiment, the single piece of material can be a metal including but not limited to, for example, surgical-grade metal alloys, stainless steel, chrome-molybdenum vanadium steel, carbon steel, titanium alloy, or the like, or a combination thereof.

The disclosure also provides a method of performing a knee arthroscopy using the patella joystick disclosed herein. In an embodiment, the method includes making an appropriate cut through the skin at an approximate center of the patella. The size of the appropriate cut can vary depending on the specific patient. In an embodiment, the size of the appropriate cut cannot be more than 50 mm. In an embodiment, the size of the appropriate cut cannot be more than 45 mm. In an embodiment, the size of the appropriate cut cannot be more than 15 mm. In an embodiment, the method also includes drilling a pilot hole in the cut. In an embodiment, the pilot hole has a diameter of at or about 2 mm. In an embodiment, the pilot hole is created by using a suitable surgical drilling tool. In an embodiment, the surgical drilling tool drills into the knee cap at a depth of 2 to 20 mm. In an embodiment, the depth is not more than at or about 10 mm. In an embodiment, the method includes securing the patella joystick 100 or 300 into the pilot hole by rotating and inserting the patella joystick 100 or 300 into the knee cap. Once the patella joystick 100 or 300 is affixed onto the knee cap, the operator can hold the patella joystick 100 or 300 to tilt and/or lift the knee cap for performing an arthroscopy procedure such as, for example, subchondral drilling or debriding cartilage of the knee cap. The operator can hold the handle 200 or the shank portion 101a of the patella joystick 100 or 300 to tilt and/or lift the knee cap. It will be appreciated that one or more of the features may be optional in an embodiment. For example, the pilot hole can be optional in an embodiment.

ASPECTS

It is appreciated that any of aspects 1-20 can be combinable to any of aspects 21-27.

Aspect 1. A patella joystick for knee arthroscopy, comprising an elongated body including a shank portion and a screw portion,
wherein the screw portion includes a thread and a screw point.

Aspect 2. The patella joystick of aspect 1, wherein the elongated body further includes a tapered portion disposed between the shank portion and the screw portion.

Aspect 3. The patella joystick as in any one of aspects 1 and 2, further comprising a handle.

Aspect 4. The patella joystick as in any one of aspects 1-3, wherein the elongated body is irremovably or removably attached to the middle of the handle, and the handle includes an elongated body or knob.

Aspect 5. The patella joystick as in any one of aspects 1-4, wherein the screw point has an inverted cone shape.

Aspect 6. The patella joystick as in any one of aspects 1-5, wherein the screw point has a point angle of at or about 90°.

Aspect 7. The patella joystick as in any one of aspects 1-6, wherein the screw portion has a length in a range of at or about 3 mm to at or about 70 mm.

Aspect 8. The patella joystick as in any one of aspects 1-7, wherein the thread has a depth in a range of at or about 0.1 mm to at or about 2 mm.

Aspect 9. The patella joystick as in any one of aspects 1-8, wherein the thread has a pitch in a range of at or about 0.1 mm to at or about 5 mm.

Aspect 10. The patella joystick as in any one of aspects 1-9, wherein the thread has a buttress thread form.

Aspect 11. The patella joystick as in any one of aspects 1-10, wherein the screw portion has a cut at the distal end thereof.

Aspect 12. The patella joystick as in aspect 11, wherein the cut forms a flute having a cutting edge.

Aspect 13. The patella joystick as in any one of aspects 2-13, wherein tapered portion includes a frustum including a first end and a second end opposing the first end, and the first end faces and joins the shank portion.

Aspect 14. The patella joystick as in aspect 13, wherein the frustum has a truncated cone shape with a cone angle of at or about 20° to at or about 89°.

Aspect 15. The patella joystick as in any one of aspects 13-14, wherein the second end of the frustum has a diameter of at or about 5 mm to at or about 20 mm.

Aspect 16. The patella joystick as in any one of aspects 11-15, wherein the frustum has a length of 1 mm to 150 mm along the elongation dimension of the frustum.

Aspect 17. The patella joystick as in any one of aspects 1-16, wherein the shank portion has a diameter or thickness of 2 mm to 20 mm.

Aspect 18. The patella joystick as in any one of aspects 2-17, wherein the shank portion and the tapered portion has a total length of at or about 10 mm to at or about 150 mm.

Aspect 19. The patella joystick as in any one of aspects 3-18, wherein the handle has a length of at or about 60 mm to at or about 200 mm.

Aspect 20. The patella joystick as in any one of aspects 3-19, wherein the handle includes a rod.

Aspect 21. A method of performing a knee arthroscopy, comprising
screwing the patella joystick of aspects 1-20 onto a knee cap.

Aspect 22. The method of aspect 21, further comprising: drilling a pilot hole at the knee cap.

Aspect 23. The method of aspects 21 and 22, further comprising performing a cut through the skin at an approximate center of a patella.

Aspect 24. The method of aspects 22-23, wherein the pilot hole has a diameter of at or about 2 mm.

Aspect 25. The method of aspects 22-24, wherein the pilot hole has a depth of not more than 20 mm.

Aspect 26. The method of aspects 22-25, further comprising holding the patella joystick to tilt and/or lift the knee cap.

Aspect 27. The method of aspects 22-26, further comprising subchondral drilling or debriding on the cartilage of the knee cap.

With regard to the preceding description, it is to be understood that changes may be made in detail, especially in matters of the construction materials employed and the shape, size, and arrangement of parts without departing from the scope of the present disclosure. This Specification and the embodiments described are exemplary only, with the true scope and spirit of the disclosure being indicated by the claims that follow.

We claim:

1. A patella joystick for knee arthroscopy, comprising an elongated body including a shank portion, a tapered portion, and a screw portion,
wherein the tapered portion is disposed between the shank portion and the screw portion,
the screw portion includes a thread and a screw point, and
the tapered portion includes a frustum having a first end and a second end opposing the first end, and the first end faces and joins the shank portion.

2. The patella joystick of claim 1, further comprising a handle,
wherein the shank portion irremovably or removably attaches to the handle.

3. The patella joystick of claim 1, wherein the screw point has an inverted cone shape, and the screw point has a point angle of at or about 90°.

4. The patella joystick of claim 1, wherein the screw portion has a length of at or about 3 mm to at or about 70 mm, the thread has a depth of at or about 0.1 mm to at or about 2 mm, and the thread has a pitch of at or about 0.1 mm to at or about 5 mm.

5. The patella joystick of claim 1, wherein the thread is configured to a buttress thread form.

6. The patella joystick of claim 1, wherein the screw portion has a cut at the distal end thereof, and the cut forms a flute having a cutting edge.

7. The patella joystick of claim 1, wherein the tapered portion further includes a reduced part extending from the second end of the frustum and is smaller in diameter or thickness than the second end of the frustum.

8. The patella joystick of claim 1, wherein the frustum has a vertical angle in a range of 0 to at or about 89 degrees.

9. The patella joystick of claim 1, wherein the frustum has a length of at or about 1 mm to at or about 150 mm.

10. The patella joystick of claim 1, wherein the shank portion has a diameter or thickness of at or about 2 mm to at or about 20 mm.

11. The patella joystick of claim 1, wherein the shank portion and the tapered portion have a total length from at or about 10 mm to at or about 140 mm.

12. The patella joystick of claim 2, wherein the handle includes a rod.

13. A method of performing a knee arthroscopy, comprising:
  screwing a patella joystick onto a knee cap;
  inserting an arthroscope into a knee; and
  holding the patella joystick to tilt and/or lift the knee cap for performing an arthroscopy procedure,
  wherein the patella joystick comprises an elongated body including a shank portion, a tapered portion, and a screw portion,
  the tapered portion is disposed between the shank portion and the screw portion,
  the screw portion includes a thread and a screw point, and
  the tapered portion includes a frustum having a first end and a second end opposing the first end, and the first end faces and joins the shank portion.

14. The method of claim 13, further comprising performing a cut through the skin at an approximate center of the knee cap.

15. The method of claim 14, further comprising: drilling a pilot hole at an approximate center of the knee cap.

16. The method of claim 15, wherein the pilot hole has a diameter of at or about 2 mm and a depth of not more than at or about 20 mm.

17. The method of claim 13, wherein the arthroscopy includes subchondral drilling or debriding on the cartilage of the knee cap.

18. The method of claim 13, wherein the screw point has an inverted cone shape, and the screw point has a point angle in a range from at or about 1° to at or about 160°.

19. The method of claim 13, wherein the tapered portion further includes a reduced part extending from the second end of the frustum and is smaller in diameter or thickness than the second end of the frustum.

20. The method of claim 13, wherein the thread is configured to a buttress thread form.

\* \* \* \* \*